US 6,610,087 B1

(12) United States Patent
Zarbatany et al.

(10) Patent No.: US 6,610,087 B1
(45) Date of Patent: Aug. 26, 2003

(54) ENDOLUMINAL STENT HAVING A MATCHED STIFFNESS REGION AND/OR A STIFFNESS GRADIENT AND METHODS FOR PROVIDING STENT KINK RESISTANCE

(75) Inventors: David J. Zarbatany, Ringwood, NJ (US); Ari Moskowitz, Hazlet, NJ (US); Fergus P. Quigley, Tipperary (IE); Lukas J. Hijlkema, Galway (IE)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/442,192

(22) Filed: Nov. 16, 1999

(51) Int. Cl.$^7$ ................................................. A61F 2/06
(52) U.S. Cl. .................... 623/1.32; 623/1.16; 623/1.35; 606/194
(58) Field of Search ................................. 623/1.1, 1.15, 623/1.16, 1.32, 1.35, 11.11, 12, 1.33; 606/191–200

(56) References Cited

U.S. PATENT DOCUMENTS

| | | | |
|---|---|---|---|
| 5,383,892 A | | 1/1995 | Cardon et al. |
| 5,649,949 A | | 7/1997 | Wallace et al. |
| 5,693,086 A | | 12/1997 | Goicoechea et al. ........... 623/1 |
| 5,817,126 A | | 10/1998 | Imran |
| 5,827,321 A | | 10/1998 | Roubin et al. .............. 606/195 |
| 5,827,588 A | | 10/1998 | Snyder et al. |
| 5,938,697 A | | 8/1999 | Killion |
| 5,968,091 A | | 10/1999 | Pinchuk et al. ................. 623/1 |
| 5,993,481 A | * | 11/1999 | Marcade et al. ................ 623/1 |
| 6,059,822 A | | 5/2000 | Kanesaka et al. |
| 6,102,940 A | * | 8/2000 | Robichon et al. .............. 623/1 |
| 6,146,403 A | | 11/2000 | St. Germain |
| 6,179,867 B1 | | 1/2001 | Cox |
| 6,264,682 B1 | * | 7/2001 | Wilson et al. ............. 623/1.11 |
| 6,327,772 B1 | * | 12/2001 | Zadno-Azizi et al. ......... 29/557 |

FOREIGN PATENT DOCUMENTS

| | | |
|---|---|---|
| EP | 0 796 597 | 9/1997 |
| EP | 0 830 853 | 3/1998 |
| EP | 0 880 948 | 12/1998 |
| FR | 2 765 097 | 6/1997 |
| WO | 97/46175 | 12/1997 |
| WO | 98/47447 | 10/1998 |
| WO | 98/53761 | 12/1998 |
| WO | 99/44535 | 9/1999 |
| WO | 00/19943 | 4/2000 |
| WO | 00/28921 | 5/2000 |
| WO | 00/42947 | 7/2000 |

OTHER PUBLICATIONS

International Search Report dated Feb. 6, 2001.

* cited by examiner

Primary Examiner—David J. Isabella
Assistant Examiner—Urmi Chattopadhyay
(74) Attorney, Agent, or Firm—RatnerPrestia

(57) ABSTRACT

A modular elongated stent having an overlap region where two modular components fit together, the overlap region being relatively stiff as compared to another more flexible region of the stent when the stent is in an assembled configuration, the stent further comprising a mimic region that has a stiffness essentially equivalent to the stiffness of the overlap region, to provide kink resistance. A stent having such a mimic region or otherwise stiff region and a flexible region may have a transition region between the stiff and flexible regions, such as a bridging material attached to the stent, also to provide kink resistance. A stent may have relatively stiff regions and relatively flexible regions positioned to align the flexible regions with curved regions of a body lumen when deployed within the body lumen. The stiffness of the stiff, flexible, and transition regions may be controlled by attaching material to the stent, varying the cross-sectional area of the stent components, varying the metallurgical properties thereof, and/or by varying the stent architecture. Methods for providing kink resistance by controlling stent stiffness are also disclosed. A stent having regions of different metallurgical properties is also disclosed, as are methods for creating such a stent.

16 Claims, 9 Drawing Sheets

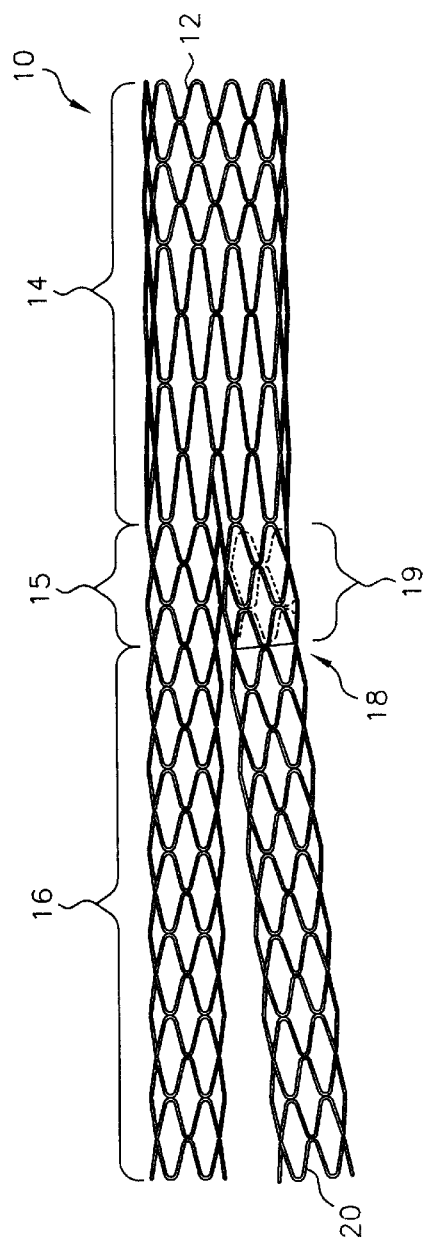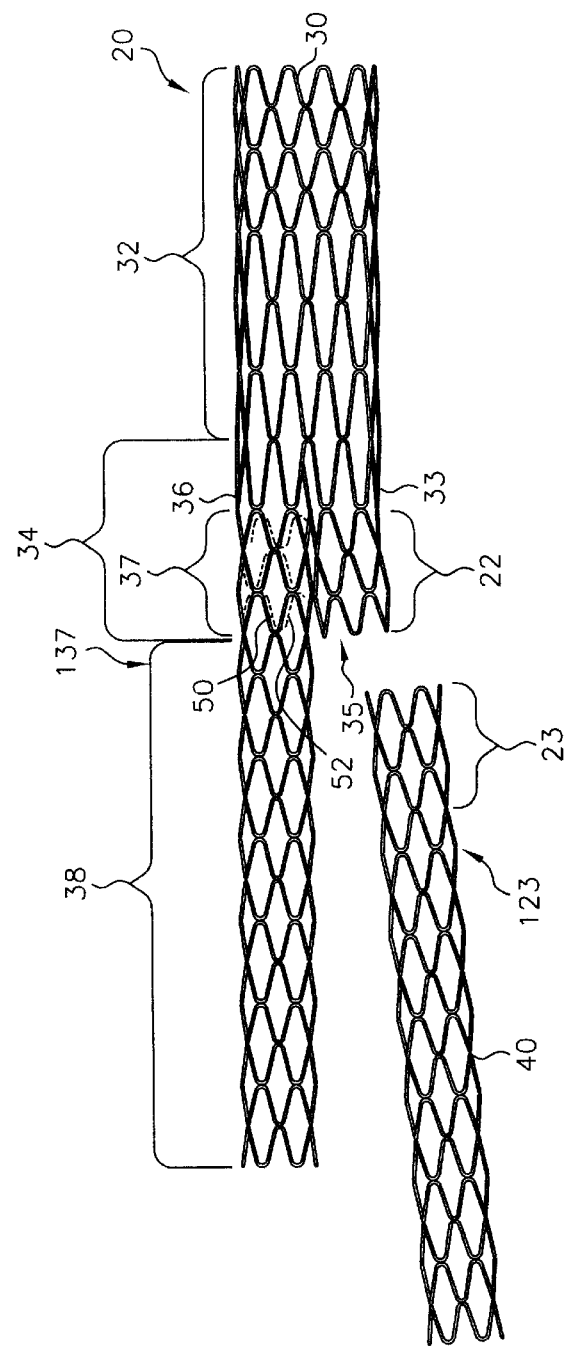

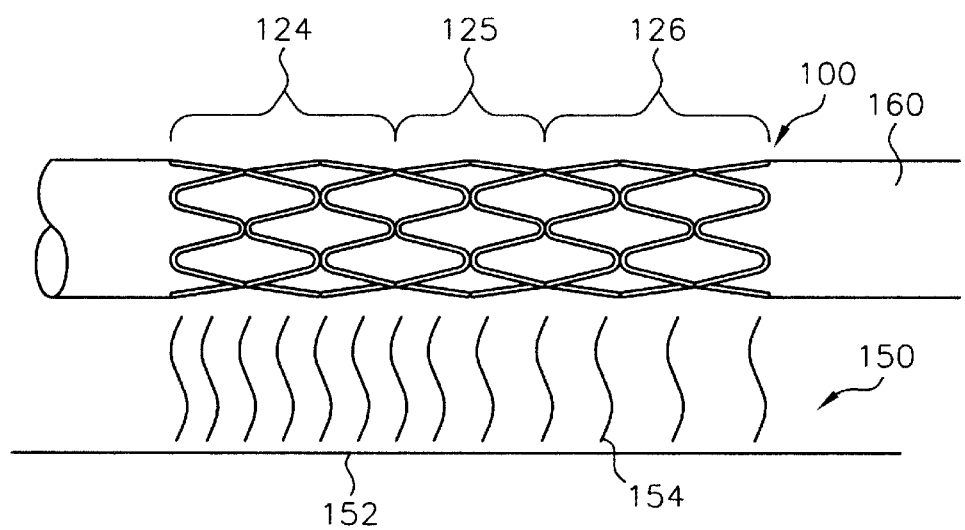
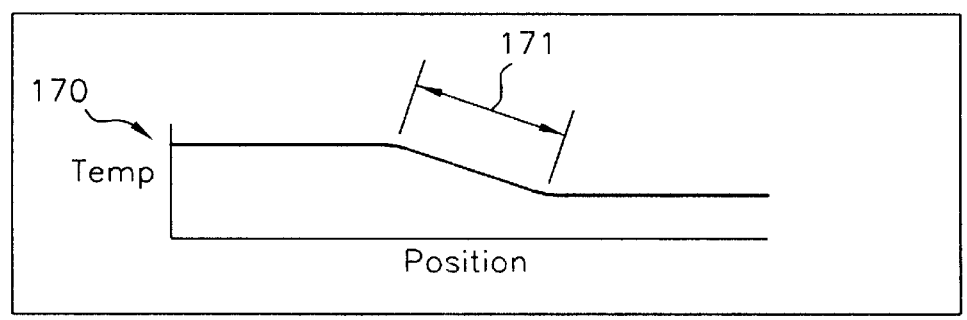
FIG. 5

ENDOLUMINAL STENT HAVING A MATCHED STIFFNESS REGION AND/OR A STIFFNESS GRADIENT AND METHODS FOR PROVIDING STENT KINK RESISTANCE

TECHNICAL FIELD

This invention relates generally to endoluminal grafts or prostheses and, more specifically, to a prosthesis having regions of different stiffness.

BACKGROUND OF THE INVENTION

A stent is an elongated device used to support an intraluminal wall. In the case of stenosis, a stent provides an unobstructed conduit for blood in the area of the stenosis. Such a stent may also have a prosthetic graft layer of fabric or covering lining the inside or outside thereof, such a covered stent being commonly referred to in the art as an intraluminal prosthesis, an endoluminal or endovascular graft (EVG), or a stent-graft.

A prosthesis may be used, for example, to treat a vascular aneurysm by removing the pressure on a weakened part of an artery so as to reduce the risk of rupture. Typically, a prosthesis is implanted in a blood vessel at the site of a stenosis or aneurysm endoluminally, i.e. by so-called "minimally invasive techniques" in which the prosthesis, maintained in a radially compressed configuration by a sheath or catheter, is delivered by a deployment system or "introducer" to the site where it is required. The introducer may enter the body through the patient's skin, or by a "cut down" technique in which the entry blood vessel is exposed by minor surgical means. When the introducer has been advanced into the body lumen to the prosthesis deployment location, the introducer is manipulated to cause the prosthesis to be deployed from the surrounding sheath or catheter in which it is maintained (or alternatively the surrounding sheath or catheter is retracted from the prosthesis), whereupon the prosthesis expands to a predetermined diameter at the deployment location, and the introducer is withdrawn. Stent expansion may be effected by spring elasticity, balloon expansion, or by the self-expansion of a thermally or stress-induced return of a memory material to a pre-conditioned expanded configuration.

Various types of stent architectures are known in the art, including many that comprise multiple regions, each region having a different stiffness, radial strength, and/or kink resistance. For example, referring now to FIG. 1, one configuration of a bifurcated modular stent 10 adapted to treat abdominal aortic aneurysms (AAA) comprises two components: a bifurcated component 12 comprising a trunk section 14 with an attached or unibody fixed ipsilateral iliac leg (IIL) 16 and a socket 18, and a second component 20 that comprises the adjoining contralateral iliac leg (CIL). When CIL 20 is connected into socket 18 as shown in FIG. 1, interface section 19 between the CIL and the socket is stiffer than interface section 15 between IIL 16 and trunk section 14. The mismatched stiffness between interfaces 15 and 19 arises in part because interface 19 comprises an overlap between the structure of leg 20 and the structure of socket 18, whereas interface 15 has no such overlapping structure.

The resulting different properties of interfaces 15 and 19 may predispose the stent to unwanted in vivo behavior such as local kinking, occlusion, or bending. Because the lumen itself into which stent 10 is placed may vary in stiffness and/or geometry, may require the stent to conform to tortuous anatomy, and/or may require the stent to accommodate bending or longitudinal or transverse deformations, it is desirable that the stent mimic the lumen and respond coherently to applied deformation or loading. Thus, it is desirable to provide a stent design that does not have local regions of mismatched stiffness such as interfaces 15 and 19 as shown in FIG. 1.

The interfaces between adjacent stent regions of different stiffness may also cause kinking, occlusion, or bending at the interface due to the drastic change in properties from one region to another. Thus, it is also desirable to minimize problems caused by abrupt stiffness interfaces between adjacent stent regions.

SUMMARY OF THE INVENTION

One aspect of the invention comprises a modular elongated stent for holding open a body lumen and for assembly in situ, the stent comprising at least a first component and a second component, the stent having an assembled configuration comprising the first component and the second component assembled together. The stent comprises an overlap region of the first component adapted to receive a portion of the second component in the assembled configuration, the overlap region having a first set of manipulation properties in the assembled configuration. One or more flexible stent regions are attached to the overlap region. Each flexible region has a second set of manipulation properties that differs from the first set of manipulation properties. The second set of manipulation properties includes greater flexibility, greater kink resistance, and/or less radial strength than the first set of manipulation properties. A mimic region is attached to the flexible region, the mimic region having a third set of manipulation properties that is essentially equivalent to the first set of manipulation properties.

The different manipulation properties may be achieved by the flexible regions and mimic region having different metallurgical properties, such as a different annealing history, by each region having structural elements of differing cross-sectional areas, or by the mimic region having reinforcing material attached thereto. The reinforcing material may comprise an overlapping stent or one or more stiffening filaments.

The modular stent may be a bifurcated modular stent in which the first component comprises a bifurcated component comprising a trunk section, a bifurcated section attached to the trunk section and having a first branch comprising a socket and a second branch comprising a fixed leg interface, and a fixed leg section depending from the fixed leg interface. In such case, the second component comprises a modular leg component adapted for insertion into the socket, the overlap region comprises the socket, the assembled configuration comprises the modular leg component inserted in the socket, and the mimic region comprises the fixed leg interface. The flexible regions comprise the trunk section and the fixed leg section.

The mimic region may comprise a region of different stent architecture relative to the flexible region, such as different element heights, different numbers of elements in each hoop, different ratios of connected to unconnected elements, or a combination thereof.

The invention also comprises a method for providing an elongated stent to hold open a designated portion of a body lumen having one or more curved regions. The method comprises first designing and fabricating the stent comprising one or more relatively stiff regions and one or more relatively flexible regions positioned to align with one of the curved regions of the body lumen when the stent is deployed within the body lumen. The relatively flexible regions have a stiffness less than the stiffness of the relatively stiff regions. Next, the stent is compressed, loaded within an introducer, and introduced into the body lumen. Finally, the stent is deployed from the introducer into the body lumen with each of the relatively flexible regions positioned in alignment with one of the curved regions of the body lumen.

Any of the stents of this invention may comprise at least one transition region between the stiff region and the flexible region having an intermediate set of manipulation properties, such as a gradient of manipulation properties, between the first set of manipulation properties and the second set of manipulation properties. The invention also comprises such a transition region between two regions having different manipulation properties wherein the transition region comprises a bridging material attached to the stent. The bridging material may comprise one or more filaments attached to the stent, such as wires welded to the stent.

The invention also comprises an elongated stent for holding open a body lumen, the stent comprising at least a first longitudinal region having first metallurgical properties and a second longitudinal region having second metallurgical properties. In particular, the different metallurgical properties may be created by providing a differential annealed history between the regions. Thus, the first metallurgical properties may be created as the result of a first annealing history and the second metallurgical properties may be created as the result of a second annealing history.

Thus, the invention comprises a method for providing kink resistance in an elongated stent adapted to hold open a body lumen, the stent having at least one stiff region with a first set of manipulation properties and at least one flexible region with a second set of manipulation properties different than the first set of manipulation properties, the second set of manipulation properties including at least one of: greater flexibility, greater kink resistance, or less radial strength than the first set of manipulation properties. The method comprises providing a mimic region having a third set of manipulation properties essentially equivalent to the first set of manipulation properties.

Providing the mimic region may comprise modifying the mimic region relative to the flexible region by modifying its local metallurgical properties, providing members having a larger cross-sectional area, attaching reinforcing material, and/or modifying the stent architecture. Modifying the metallurgical properties may comprise heat treating the mimic region, such as by local laser heat treating. Modifying the metallurgical properties may in the alternative comprise providing a different annealing history for the mimic region. Thus the invention also comprises providing an elongated stent for holding open a body lumen with a first longitudinal region having first metallurgical properties and a second longitudinal region having second metallurgical properties. The method comprises exposing the first longitudinal region to a first annealing history and exposing the second longitudinal region to a second annealing history.

Providing the different annealing history may comprise providing a zoned annealing furnace having a relatively hotter region and a relatively cooler region, and annealing the stent by exposing the flexible region of the stent to the relatively hotter region of the furnace and exposing the stiff region of the stent to the relatively cooler region of the furnace. Another method of providing the different annealing history for the mimic region comprises mounting the stent during annealing on a mandrel having a relatively high thermal conductivity region and a relatively low thermal conductivity region or a relatively high heat sink region and a relatively low heat sink region. The relatively high heat sink region or relatively high thermal conductivity region of the mandrel is co-located with the stiff region of the stent, whereas relatively low heat sink region or relatively low thermal conductivity region of the mandrel is co-located with the flexible region of the stent. Because of the relatively different heat sink or thermal conductivity properties in different portions of the mandrel, the flexible region attains a higher annealing temperature or greater thermal input/load than the stiff region. The relatively high heat sink region or relatively high thermal conductivity region tends to conduct more heat away through the mandrel than the relatively low heat sink region or relatively low thermal conductivity region. To create differential heat sink regions, the mandrel may be fabricated of a greater cross-sectional mass in the high heat sink region than in the low heat sink region. To create differential heat conductivity regions, the mandrel may be fabricated, for example, of metal in the high conductivity region and ceramic in the low heat conductivity region.

The invention also comprises a method for minimizing kinking of an elongated stent during introduction of the stent through the body lumen to a deployment location and during deployment of the stent at the deployment location. The stent has at least one stiff region with a first set of manipulation properties adjacent to at least one flexible region with a second set of manipulation properties different than the first set of manipulation properties. The second set of manipulation properties includes at least one of: greater flexibility, greater kink resistance, or less radial strength than the first set of manipulation properties. The method comprises first fabricating the stent with a transition region between the stiff region and each flexible region, the transition region having a third set of manipulation properties between the first set of manipulation properties and the second set of manipulation properties. Next, the stent is radially compressed and loaded into an introducer. Finally, the introducer is navigated through a tortuous body lumen while the transition region minimizes kinking of the stent resulting from the difference between the first set of manipulation properties and the second set of manipulation properties. The method may further comprise providing the transition region with a gradient from the first set of manipulation properties to the second set of manipulation properties.

BRIEF DESCRIPTION OF DRAWINGS

FIG. 1 is side view of a bifurcated modular stent-graft of the prior art in an assembled configuration, with the graft illustrated in a transparent format to show the stent scaffolding underneath.

FIG. 2 is a side view of a bifurcated modular stent according to the present invention in an unassembled configuration, with the graft illustrated in a transparent format to show the stent scaffolding underneath.

FIG. 5 is a schematic illustration of a stent undergoing an annealing step in a zoned annealing furnace, showing a graph of the temperature gradient in the furnace.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

A typical stent has a number of manipulation properties, such as stiffness or flexibility, radial strength, and kink resistance. As used herein, "flexibility" or stiffness can be described in terms of the amount of force required to deform a stent into an arc. For example, referring to the schematic representation in FIG. 11, the force f required to bend tubular stent 2000 of a particular length into a given arc having a central angle and a given arc radius, is a measure of the stent flexibility. Thus, comparing two stents of equal length with different stent architectures, the stent requiring greater force to bend it into a given arc is relatively stiffer, whereas the stent requiring lesser force is relatively more flexible.

Figure 11:
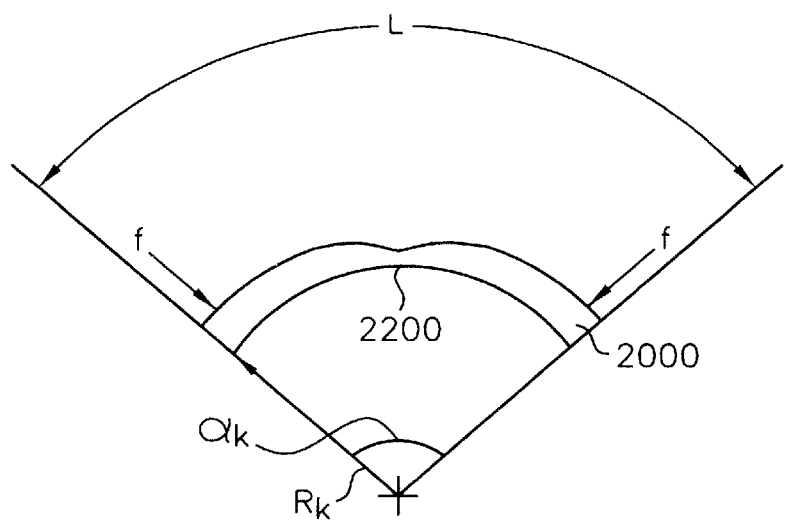
FIG. 11 is a side view schematic showing an exemplary stent being bent into an arc.

A measure of the "kink resistance" of a stent is the kink angle $\alpha_k$ or kink radius $R_k$ at which the stent kinks (when the tubular configuration becomes disrupted by crease 2200 as shown in FIG. 11). Thus, if one compares the kink angle and kink radius of one tubular stent of a length having a first stent architecture to another tubular stent having the same length but a second stent architecture, the stent architecture having a lesser kink radius and a greater kink angle has the most kink resistance.

As used herein, "radial strength" can be described generally as the resistance of a stent to radial compression. A stent with more radial strength exerts a greater outward radial force when compressed than does a stent with less radial strength. Thus, for example, a shape memory expandable or resiliently compressible stent may have a fully expanded diameter and a constrained diameter as deployed within a lumen. The fully expanded diameter is the diameter to which the stent would expand without any constraint. At the constrained diameter, the stent exerts a radial force F against the lumen, which when distributed over the surface area A of contact between the stent and the lumen can be expressed as a pressure P=F/A in force per unit area. Thus, radial strength can be expressed in terms of radial force or radial pressure. When comparing the radial strength of two stents having different stent architectures, if both stents have the same surface area A of contact (which is the same as having the same contact length where the diameters are equal), radial force is a valid measure of radial strength. If one stent has a different surface area than the other, however, then radial pressure is a more appropriate measure of radial strength, so that the surface area of the stent is not a factor in the comparison.

The specification and claims use the terms "stent architecture" and "geometric configuration" throughout. As used herein, "stent architecture" refers to the various structural elements that comprise the stent construction. There are general categories of architecture, such as for example, wound stent architecture, braided stent architecture, laser cut tube stent architecture, filamentary stent architecture, polygonal cell stent architecture, or zig-zag stent architecture. The various categories of stent architecture may overlap one another. For instance, one stent may comprise a filamentary, wound, polygonal cell stent architecture, whereas another stent may comprise a laser cut tube, polygonal cell stent architecture. "Filamentary" indicates that a stent comprises one or more filaments formed into the stent architecture, whereas a "laser cut tube" indicates that the stent comprises a tube that has been cut by a laser to form the geometric elements. Although there are numerous broad categories of stent architecture, within each broad category there are a number of stent architectures that are considered "different" for the purposes of this specification and claims. For example, one region of a stent having a certain height geometric element may be considered a first stent architecture whereas another region of the same stent having a similar geometric element of a different height may be considered a second, different stent architecture. Other differences in architecture from one region to another may include, for example, the number of elements in each hoop or the ratio of connected to unconnected elements.

One component of stent architecture is geometric configuration. The "geometric configuration" refers to the geometric shape of the elements created within the stent. Thus, for instance, a stent having a filamentary, wound, polygonal cell stent architecture may have a geometric configuration wherein the cells are hexagonal and have a first size. Another stent having hexagonal cells of a second size still has the same geometric configuration as the stent having the hexagonal cells of the first size, but may still be said to have a different stent architecture.

Stiffness (or flexibility), kink resistance, and radial strength are somewhat interrelated, in that for a given stent architecture, a design having a greater stiffness (and thus, lesser flexibility) generally has greater radial strength and less kink resistance as well. Although the three properties are interrelated, however, they are not necessarily proportionally or linearly related. That is, a first stent having 20% greater stiffness than a second stent may not necessarily have 20% greater radial strength or 20% less kink resistance, despite having some greater degree of radial strength and some lesser degree of kink resistance. Also, a particular stent architecture may have, as an inherent function of its design, both greater stiffness and greater kink resistance as compared to another stent architecture. Because these properties are somewhat interrelated to one another and they all relate to reaction of the stent to manipulation (bending or radially compressing), the term "manipulation property" is used herein to designate any one or more of these properties to facilitate discussion of this invention. Additionally, examples of different regions having different manipulation properties are discussed herein primarily in terms of variation in flexibility or stiffness. It should be understood, however, that whereas one stent region with respect to another may be characterized for brevity and convenience herein with respect only to differing stiffness, that region may also have a different radial strength and/or kink resistance as well.

Referring now to FIG. 2, stent 20 is a modular bifurcated stent essentially identical to the stent shown in FIG. 1 except for a modification according to the present invention. Stent 20, shown in its unassembled configuration, has two modular components: bifurcated component 30 and modular leg component 40. Bifurcated component 30 comprises a trunk section 32, a branching section 34 and a fixed leg section 38. Branching section 34 has a first branch 33 comprising a socket 35 and a second branch 36 comprising a fixed leg interface 37, from which fixed leg section 38 depends. In the assembled configuration of the stent 20, similar to the assembled configuration of stent 10 shown in FIG. 1, mating portion 23 of modular leg component 40 inserts into socket 35, creating a stiff, overlap in region 22. Although overlap region 22 is not shown in an assembled configuration (with mating portion 23 of leg 40 inserted in socket 35) in FIG. 2, it should be understood that any reference herein to overlap region 22 and properties thereof refer to overlap region 22 in the assembled configuration of modular stent 20 (which resembles the assembled configuration of stent 10 shown in FIG. 1). Modular leg component 40 may mate with socket 35 in any known way to create such an overlap 22. Trunk section 32 and fixed leg section 38 comprise relatively flexible regions that are less stiff than overlap region 22.

Unlike stent 10 shown in FIG. 1, however, fixed leg interface 37 of stent 20 comprises a reinforced region that mimics the manipulation properties of overlap region 22 in accordance with the present invention. Although the purpose of reinforcing fixed leg interface 37 is to provide essentially the same manipulation properties in both the reinforced region and in the overlap region 22, it should be understood that in practice, due to variations in materials, assembly, or other factors, the actual manipulation properties of the overlap region and reinforced region may not be exactly the same. The manipulation properties of the two regions are "essentially equivalent" as claimed herein, however, in that fixed leg interface 37 reacts to loading in the same manner as overlap region 22. In particular, fixed leg interface 37 being essentially equivalent to overlap region 22 means that whatever slight differences may remain between the two regions, these differences are not significant enough to cause kinking merely as a result of any mismatch between the manipulation properties of the two sides.

As shown in FIG. 2, fixed leg interface 37 comprises reinforcing material attached to stent 20 in the form of an overlapping stent 50. Although the reinforcing material shown in FIG. 2 comprises a discrete overlapping stent 50 having filaments 52 arranged in a pattern similar to overlap region 22, in an alternative embodiment the stiffening filaments 52 attached to stent 20 may be individual filaments rather than forming a discrete and separate stent. Other means for stiffening a region to mimic another region may also be used, as are described below. Because the manipulation properties of fixed leg interface 37 match those of overlap region 22, opposite branches 33 and 36 of branching section 34 respond more coherently to applied deformation or loading, mimic the lumen tortuosity better, and are more resistant to kinking, occlusion, or bending than in a stent such as stent 10 shown in FIG. 1 having mismatched manipulation properties on opposite branches.

With fixed leg interface 37 and overlap region 22 having essentially matched properties in accordance with this invention, regions 137 and 123 just below interface 37 on leg 38 and mating portion 23 on leg 40, respectively, as shown in FIG. 2 become the next regions most likely to kink. Accordingly, the invention may further comprise regions 137 and 123 that have a greater stiffness than the remainder of leg 38 and leg 40, respectively, to prevent kirking in those regions. The stiffening in regions 137 and 123 may be effected by any of the methods discussed herein below.

Although discussed with respect to FIGS. 1 and 2 in terms of a bifurcated modular stent, non-bifurcated modular stents also have overlap regions that may benefit from providing a mimic region elsewhere in the stent to match the manipulation properties of the overlapping region of the stent. Many stent embodiments have multiple regions with different manipulation properties, such as higher radial strength sections at the ends of a stent, that do not necessarily mimic other regions of the stent. Regardless of how or why such regions are created, another aspect of this invention addresses the discontinuity of manipulation properties that arises between adjacent stiff and flexible regions.

Figure 3:
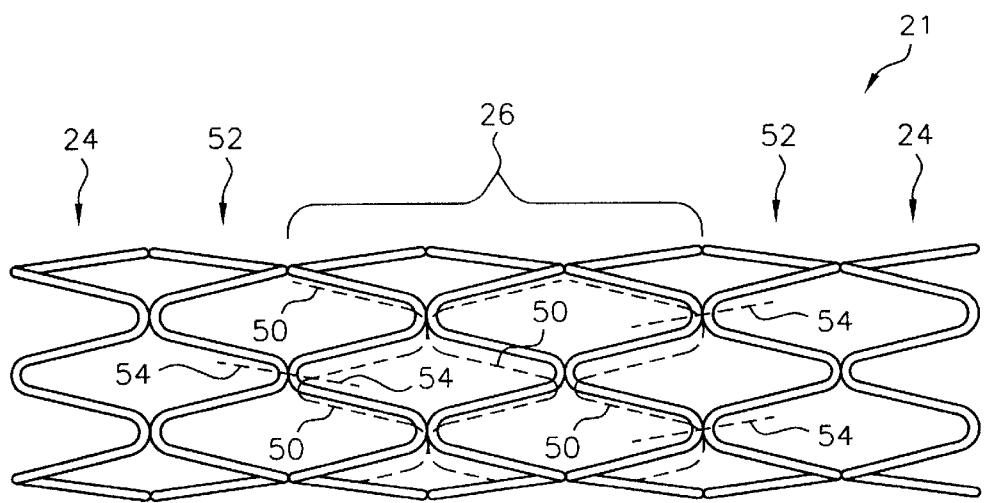
FIG. 3 is a side view of a portion of a stent showing a reinforced region and a transition region between the reinforced region and adjacent flexible regions.

Referring now to FIG. 3, there is shown a portion of a stent 21 having a relatively stiff, reinforced region 26 (or mimic region) and relatively more flexible regions 24, and further comprising a transition region 52 between reinforced region 26 and flexible regions 24. Transition regions 52 have intermediate manipulation properties, such as greater stiffness than in flexible regions 24 and less stiffness than in mimic region 26. Transition region 52 may comprise a gradually increasing stiffness (i.e., a gradient) from the flexible region 24 to the mimic region 26 as one travels along the length of transition region. Thus, as used herein, an "intermediate" property of a transition section is a property between the two sections on either end of the transition section, with the property retaining the same value along the length of the transition section or gradually changing along the length of the transition section, as a gradient.

As shown in FIG. 3, transition region 52 may comprise a bridging material, such as a plurality of bridging filaments 54, attached to the stent. Stent 21 as shown in FIG. 3 is a wound stent, such as a wire stent comprising nitinol wires. Thus, filaments 54 may typically comprise metal wires, such as nitinol, welded to the stent, but may comprise other filaments known in the art such as polymeric filaments, and may be attached by other means such as adhesive bonding, suturing, or other methods known in the art. The bridging filaments create a "force bridge" that provides a stiffness gradient between the flexible region 24 and the reinforced region 26, dampening the step-change in stiffness. Other means for providing a transition region having intermediate manipulation properties or a gradient of manipulation properties may also be used, however, some examples of which are discussed herein later.

Returning now to FIG. 2, stiffened region 137 on leg 38 may thus be a transition region of intermediate stiffening between the relatively greater stiffening desired for fixed leg interface 37 to mimic overlap region 22 and the normal flexibility of the remainder of leg 38. Stiffened region 123 therefore essentially mimics transition region 137, as region 123 stands alone without any corresponding region of greater stiffness on leg 40 to transition from, as the greater stiffness in overlap region 22 arises only after mating portion 23 is inserted in socket 35. Accordingly, region 123 may be referred to as a "transition mimic" region.

Thus, the invention encompasses any stent having a transition region at an interface between regions of differing manipulation properties, such as a transition region between a stiff region and a flexible region to provide an intermediate stiffness, including a stiffness gradient. The transition region may comprise any of the various means for providing a transition, as disclosed herein. Furthermore the invention includes providing kink resistance to a stent having regions of different manipulation properties by providing a transition region between the different regions.

One means of providing regions having different manipulation properties within a stent is to provide regions having different metallurgical properties. As used herein, the term metallurgical property shall have its common meaning, namely a characteristic of a metal including both how the metal was made and its physical and chemical characteristics. Different metallurgical properties, as used herein, are sufficiently different such that some measurable difference in manipulation properties can be seen in a typical use of the prosthesis of the present invention.

Figure 4:
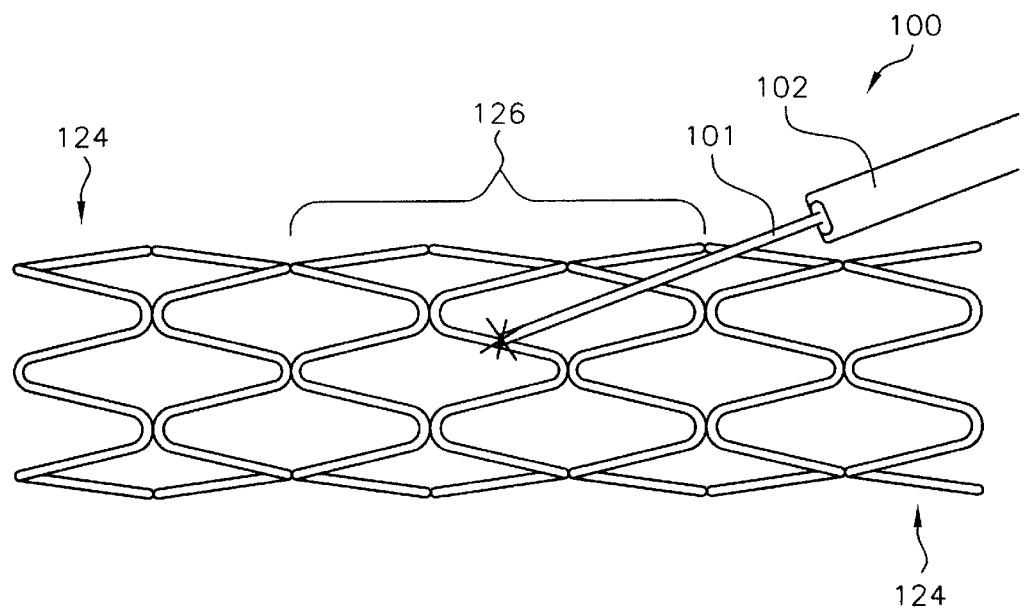
FIG. 4 is a schematic illustration of a stiff portion of a stent receiving a laser heat treatment.

As shown in FIG. 4, a stiff region 126 of stent 100 may receive a localized heat treatment, such as from a beam 101 of laser device 102, that modifies the metallurgical properties in the stiff region to make it stiffer than the metallurgical properties in remaining flexible region 124. For example, a high-power laser, such as a continuous wave YAG or $CO_2$ laser, may be focused on a small area of the stent wire or scanned over the length of the wire (or the wire may be moved through the laser's focal point). A temperature between 100° C. and the melting point of the alloy, controlled by varying the power of the beam and the exposure time (for example, on the order of approximately 1 second), may be sufficient to create the desired modification in metallurgical properties.

Another method of providing different metallurgies to different regions is to anneal each region using different amounts of thermal input, thus providing a different annealing history for each region. In particular, where stent 100 comprises a nitinol stent, the annealing history of the metal sets the material and shape memory properties of the stent, as is well known.

The different annealing histories may be provided in any number of ways, three exemplary methods of which are described herein. The effect of the annealing process on the wire of the stent is dependent upon the product of temperature and time, referred to herein as the "thermal input". Because the mandrel and stent are typically relatively cold when put in a hot annealing furnace, there is a certain amount of heat-up time during which the stent is exposed to a gradually increasing temperature until reaching an equilibrium temperature, and thus the thermal input typically takes the form of a time integral of temperature. The thermal input necessary to create the desired properties in a wire is dependent upon the material composition of the wire, the diameter of the wire, and the cold-working or strain history of the wire. Accordingly the precise temperatures and times of exposure vary depending upon the pre-annealed and desired annealed properties of the wire, but are known by those skilled in the art for specific wire grades commonly used and are readily determinable for new wire grades by experimentation.

In one method, illustrated in FIG. 5, a zoned annealing furnace 150, such as is well-known in the art, is used to provide a relatively hotter region 152 and a relatively cooler region 154, as illustrated by the temperature/position curve shown in graph 170. Stent 100 is annealed on mandrel 160 by exposing flexible region 124 of the stent to relatively hotter region 152 of furnace 150 and exposing stiff region 126 of the stent to relatively cooler region 154 of the furnace. Annealing stent 100 for a predetermined amount of time with such exposures thus provides flexible region 124 with a greater thermal input than stiff region 126. Because the furnace has a temperature gradient 171 between relatively hotter region 152 and relatively cooler region 154, stent 100 further comprises a transition region 125 having a gradient of metallurgical properties from flexible region 124 to mimic region 126. For example, a 3-zone tube furnace, marketed by Carbolite of Sheffield, England, can supply up to three different temperature zones, each 200 mm long, with a maximum differential of 30° C. between each pair of adjacent zones. A 30° C. temperature differential is sufficient to produce desired differences in manipulation properties across corresponding regions in the stent and gradient intermediate properties between the regions. Although illustrated in FIG. 5 with only 2 temperature zones and 2 corresponding regions of the stent, it should be understood that a stent according to the present invention may be made with as many different zones as can be supplied by the annealing furnace, including more than 3 zones.

Figure 6A:
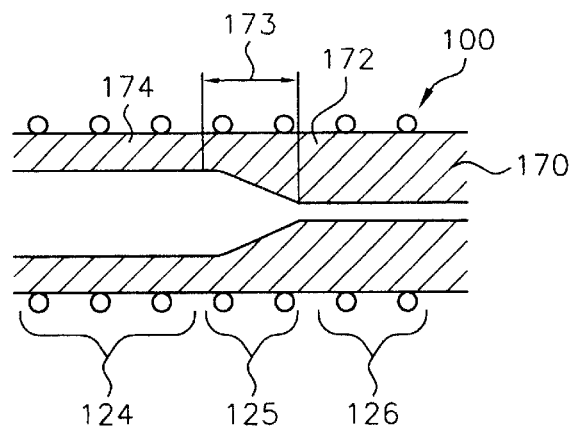
FIG. 6A is a cross-sectional illustration of a stent mounted on an exemplary mandrel having a variable conductive mass per unit length.

Referring now to FIG. 6A, another method of providing a different annealing history for the stiff region 126 versus the flexible region 124, is to provide a hollow mandrel 170 that has a high heat sink region 172 and a low heat sink region 174. High heat sink region 172 has a relatively higher thermally conductive mass per unit length than low heat sink region 174. For example, as shown in FIG. 6A, high heat sink region 172 may comprise a region having a greater cross-sectional mass than the low heat sink region 174. High heat sink region 172 of the mandrel 170 is co-located with stiff region 126 of stent 100 and low heat sink region 174 of mandrel 170 is co-located with flexible region 124 of the stent.

During annealing, the thermal inertia provided by high heat sink region 172 as compared to low heat sink region 174, provides for a longer heat-up time in the high heat sink region that keeps stiff region 126 from experiencing as much thermal input as flexible region 124. Therefore, for example, although both regions 172 and 174 may ultimately reach the temperature of the annealing furnace by the end of the exposure time in the furnace, high heat sink region will reach that temperature at a slower rate, and thus the time integral of temperature is less in the high heat sink region than in the low heat sink region. Transition region 173 between the cross-sectional mass in the high heat sink region and the cross-sectional mass in the low heat sink region may comprise a gradual change in cross section to provide a thermal input gradient and a corresponding gradient of metallurgical properties in transition region 125 of stent 100.

Figure 6B:
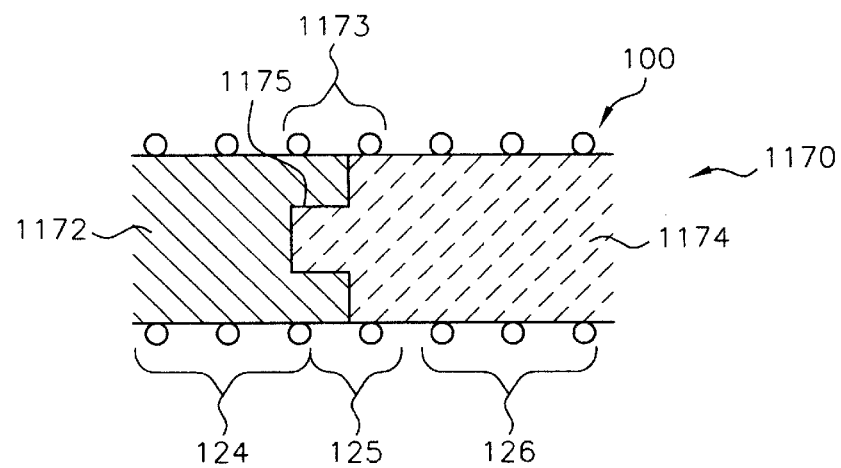
FIG. 6B is a cross-sectional illustration of a stent mounted on an exemplary mandrel having two sections, each section differing in materials of construction and thermal conductivity.

In the alternative, referring now to FIG. 6B, region 1172 of mandrel 1170 may have a higher thermal conductivity (greater specific heat capacity) than region 1174. For example, region 1172 may be metal and region 1174 may be ceramic. In such case, the greater thermal conductivity of region 1172 as compared to region 1174 of mandrel 1170 subjects flexible region 124 of stent 100 to a greater thermal input than stiff region 126, which creates the difference in annealed stiffness. The greater thermal conductivity allows a faster heat-up time and thus a greater time integral of temperature. For example, stainless steel (alloy 304 SS) has a thermal conductivity of approximately 16 W/mK (Watts per meter per degree Kelvin), aluminum has a conductivity of approximately 147 W/mK, and toughened zirconia ceramic has a conductivity of approximately 2 W/mK. Mandrel 1170 thus may comprise a mix of adjacent ceramic and metallic regions. A threaded fitting or adhesively-bonded post 1175 may be provided at the interface between the regions, thus creating a transition region 1173 having an intermediate thermal conductivity that creates transition region 125 in stent 100. In the alternative, another material with an intermediate thermal conductivity could be used in the transition region. The geometry of post 1175 (or omission of the post altogether) may be manipulated as desired to tailor the thermal conductivity in the transition region between that of a step change and a gradient.

Figure 6C:
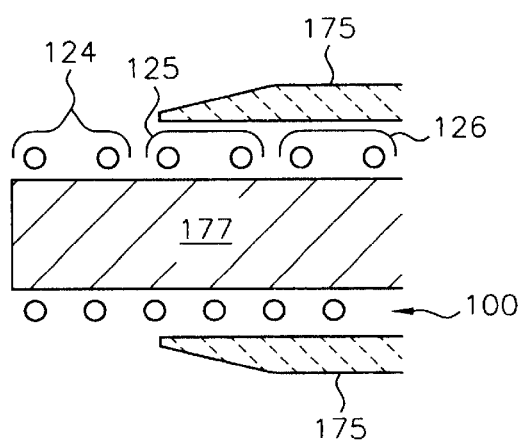
FIG. 6C is a cross-sectional illustration of a stent mounted on a mandrel and partially covered with a shielding collar.

In yet another alternative embodiment, shown in FIG. 6C, a collar 175 of ceramic material may be placed over stiff region 126 of the stent on an all-metallic mandrel 177 during annealing, shielding the stent wire in stiff region 126 from some of the heat of the annealing furnace (or other annealing heat source known in the art). Collar 175 may have a variable thickness to provide a transition region 125 between flexible region 124 and stiff region 126. The variable thickness may be in the form of a gradient thickness as shown in FIG. 6C, or may comprise a step change in thickness. In the alternative, different collars having different thicknesses and/or different thermal conductivities may be used for the stiff region 126 and the transition region 125. Rather than a single collar with variable thickness as shown in FIG. 6C, the transition region may in the alternative be provided using multiple collars having different thicknesses and/or materials of construction or gradients thereof.

Figure 7:
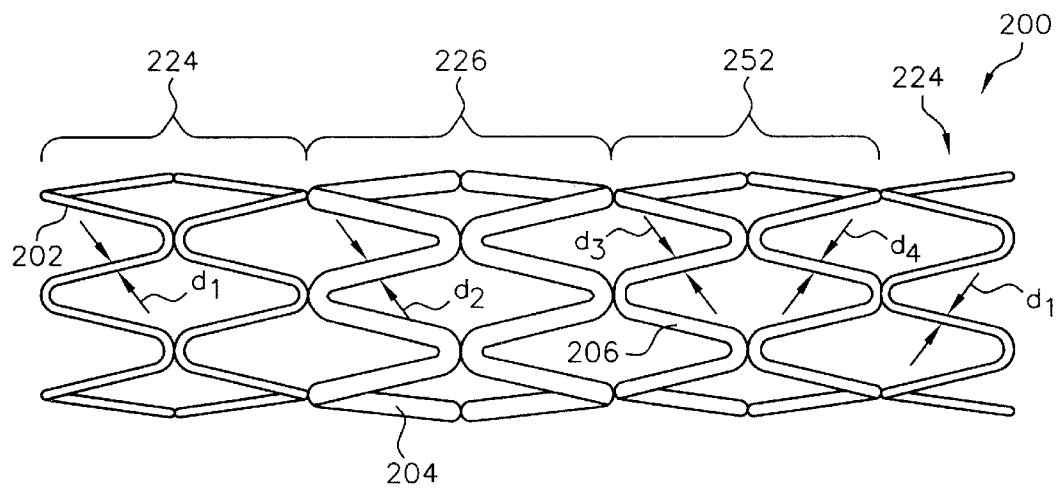
FIG. 7 is a side view of a portion of a wire stent having multiple wire diameters.

Another way for providing regions of a stent having different manipulation properties is to vary the cross-sectional area of the structural elements of the stent. Thus, referring now to FIG. 7, for a metal wire stent 200, wire 202 in flexible region 224 may have a smaller diameter $d_1$ than wire 204 in the stiff region 226 having a diameter $d_2$. For non-wire stents, such as laser-cut tubular stents, the metal left between the laser-cut slots may be thicker in the stiff region than in the flexible region. Where it is desired to provide a gradient in manipulation properties from one region to another, wire 206 in transition region 252 may be an intermediate thickness $d_3$, or wires 202, 204, and 206 may together form a continuous wire having a diameter gradient between flexible region 224 and stiff region 226 decreasing from $d_4$ to $d_3$ to $d_2$ to $d_1$.

Figure 8:
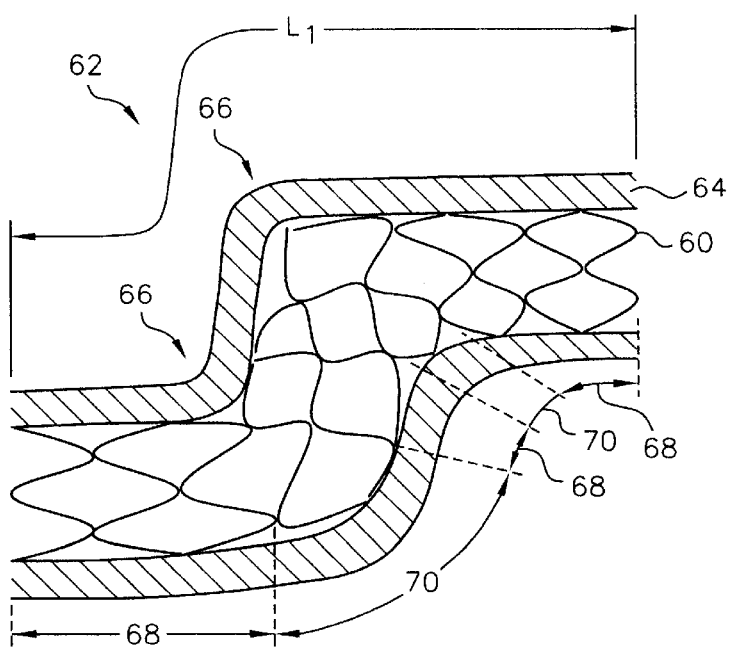
FIG. 8 is a cross section of a tortuous lumen having a stent mounted therein.

The embodiments described above relating to modifying the metallurgical properties or the cross-sectional area of the stent wire in certain regions to provide more stiffness are also well suited for use in reverse to provide more flexible areas. For example, referring now to FIG. 8, there is shown an elongated stent 60 for holding open designated portion 62 of body lumen 64 having curved regions 66. Designated portion 62 has a length $L_1$. Stent 60 has an expanded configuration for deployment within the body lumen as shown in FIG. 8, a compressed configuration (not shown) for introduction and transport within the lumen prior to deployment as is well-known in the art, and a length equivalent to length $L_1$. Stent 60 has relatively stiff regions 68 and relatively flexible regions 70, each of the flexible regions positioned to align with one of the curved regions 66 of the body lumen 64 when stent 60 is deployed. Given a standard stiffness for a certain stent design, relatively flexible regions 70 may be tailored by reducing the cross sectional area of the stent or by providing a higher annealing temperature, rather than tailoring relatively stiff regions 68 by increasing the cross-sectional area or providing a lower annealing temperature.

Figure 9:
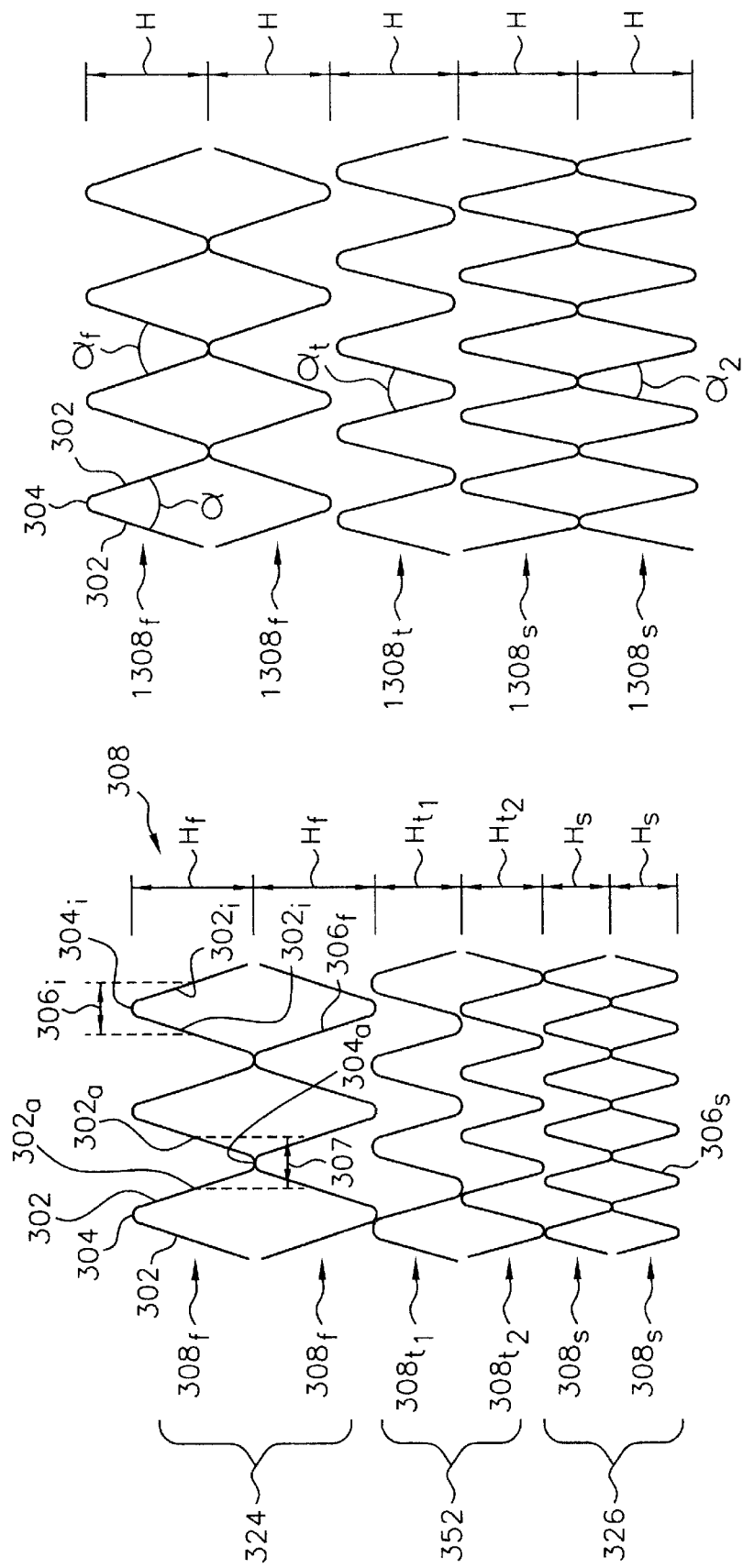
FIG. 9A is a plan view of an exemplary stent embodiment cut along a line parallel to the stent axis and flattened, showing a stent having a modified stent architecture creating a stiff region and a transition region.
FIG. 9B is a plan view of another exemplary stent embodiment cut along a line parallel to the stent axis and flattened, showing a stent having a modified stent architecture creating a stiff region and a transition region.
Figure 10:
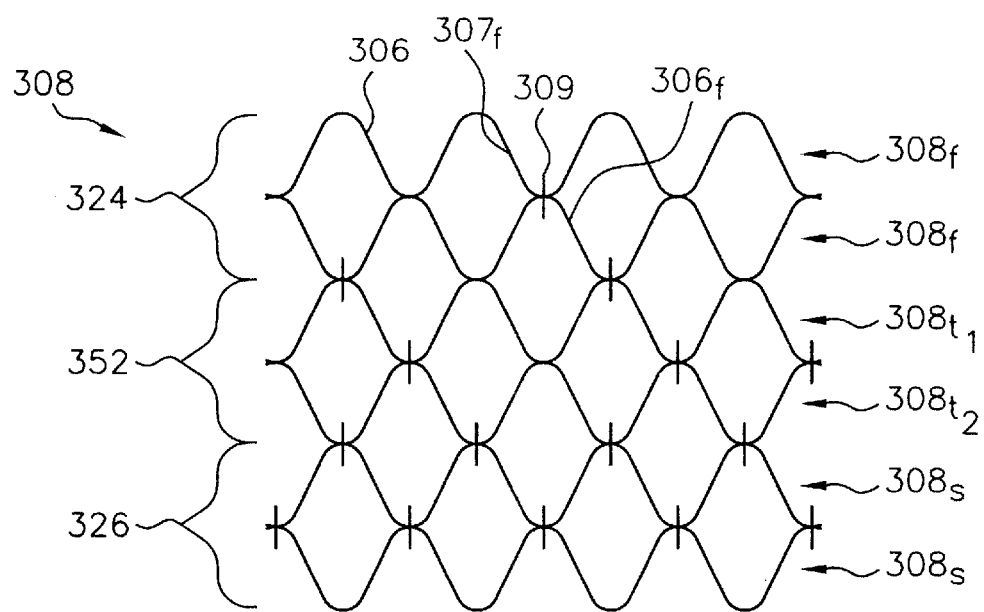
FIG. 10 is a plan view of an exemplary stent embodiment where the stent has been cut along a line parallel to the stent axis and laid flat, showing a stent having a modified ratio of connected to unconnected apex sections to create a stiff region and a transition region.

Modifying stent architecture may also be used for providing regions of different manipulation properties within a stent to mimic another region of the stent and/or to provide kink resistance. For example, as shown in FIGS. 9A, 9B, and 10, the stent may have a stent architecture comprising a recurrent pattern of geometric elements—struts 302 connected at apex sections 304 to form zigs 306 and zags 307, each zig comprising apex section 304$i$ and the top half of connected struts 302$i$ pointing in one direction (down, as shown in FIG. 9A) and each zag comprising an apex section 304$a$ and the bottom half of connected struts 302$a$ pointing in the opposite direction (up, as shown in FIG. 9A). The elements are arranged in circumferential hoops 308 axially attached to one another. Although shown in FIGS. 9A and 9B as circumferential hoops 308 and 1308 normal to the axis of the stent, a hoop in a helical winding pattern may comprise one 360° helical revolution of the wire about the stent. Each zig in hoop 308$f$ of flexible section 324 as shown in FIG. 9A has a zig height $H_F$. Each hoop 308$f$ has three zigs per hoop. Stiff region 326 has hoops 308$s$ having a zig height $H_s$ that is less than zig height $H_F$ and having six zigs 306$s$ per hoop. Transition region 352 provides a gradient of manipulation properties between flexible region 324 and stiff region 326 by providing zigs of an intermediate zig height, namely in a gradient from $Ht_1$ in hoop 308$t_1$ to $Ht_2$ in hoop 308$t_2$, and by providing an intermediate number of elements in each hoop, namely 4 zigs in hoop 308$t_1$ and 5 zigs in hoop 308$t_2$. Although shown in FIG. 9A with both the height and number of zigs varied from the flexible to the stiff region, alternate embodiments may vary only a single variable, such as is shown in FIG. 9B.

Where only the number of zigs is varied as shown in FIG. 9B, or where only the zig height is varied (not shown), the included angle $\alpha$ between adjacent struts 302 also varies from hoop to hoop. As shown in FIG. 9B, where the number of zigs varies from 4 zigs in hoops 1308$f$ to 6 zigs in hoops 1308$s$, with 5 zigs in transition hoop 1308$t$, the included angle $\alpha_f$ in hoops 1308$f$ is greater than the included angle $\alpha_t$ in hoop 1308$t$ which, in turn, is greater than the included angle $\alpha_s$ in hoops 1308$s$. Thus, the included angle is another variable that may be varied, not only with respect to continuous wire zig-zag elements as illustrated in FIGS. 9A and 9B, but also with respect to elements of other stent architectures as well, such as laser-cut tubular stent architectures. Where both the zig height and zig number are varied, as shown in FIG. 9A, the included angle may or may not vary, depending upon the specific variation of zig height and zig number.

One or more zigs 306 in each hoop 308 may be connected to an axially adjacent hoop 308, such as with a suture 309 as shown in FIG. 10. A weld, an adhesive bond, or any means known in the art for joining axially adjacent elements may be provided. In hoop 308$f$ in flexible region 324 of FIG. 10, only one zig 306$f$ is axially connected to a zag 307$f$ of the axially adjacent hoop, providing a ratio of 1:3 connected to unconnected zigs (25% connected zigs) in the flexible region. In stiff region 326, 100% of the zigs are connected. Transition region 352 provides a stiffness gradient between flexible region 324 and stiff region 326 by providing an intermediate ratio of connected to unconnected elements, namely a ratio gradient comprising 2:2 in hoop $308t_1$ and 3:1 in hoop $308t_2$.

Although for clarity, FIG. 9A illustrates a varied zig height plus a varied number of zigs per hoop, FIG. 9B illustrates a varied number of zigs only, and FIG. 10 illustrates the varied connected to unconnected ratio only, a single stent embodiment may incorporate variations of any combination of the above variables. Although discussed herein with respect to a zig-zag wire stent architecture, other stent architectures having elements with a different geometry may comprise regions of different size elements, different numbers of elements per hoop, different angles between structural members, or different ratios of connected elements, to provide similar variations in manipulation properties.

In the embodiments shown herein, the stiff and the flexible regions have the same general stent geometry. That is, although certain features of the architecture may be changed, such as zig height, number of zigs, or ratio of connected to unconnected zigs, the general zig-zag geometry is still maintained. In other stent designs, such as those described in co-pending application [Ratner & Prestia docket number BSI-400] to Paul Chouinard and Pat Haverkost filed on the same day as the present application and assigned to the common assignee of this invention, incorporated herein by reference, two entirely different filamentary stent geometries may be linked together, such as a braided stent geometry and a zig-zag stent geometry. Each geometry has respective manipulation properties, and thus the interface between regions of different geometry, in certain configurations, may present a distinct step change. Thus, the present invention of providing a transition region between a relatively stiff and a relatively flexible region may be incorporated into such a design, such as by attaching wires as force bridges between the different stent geometry regions.

Figure 12:
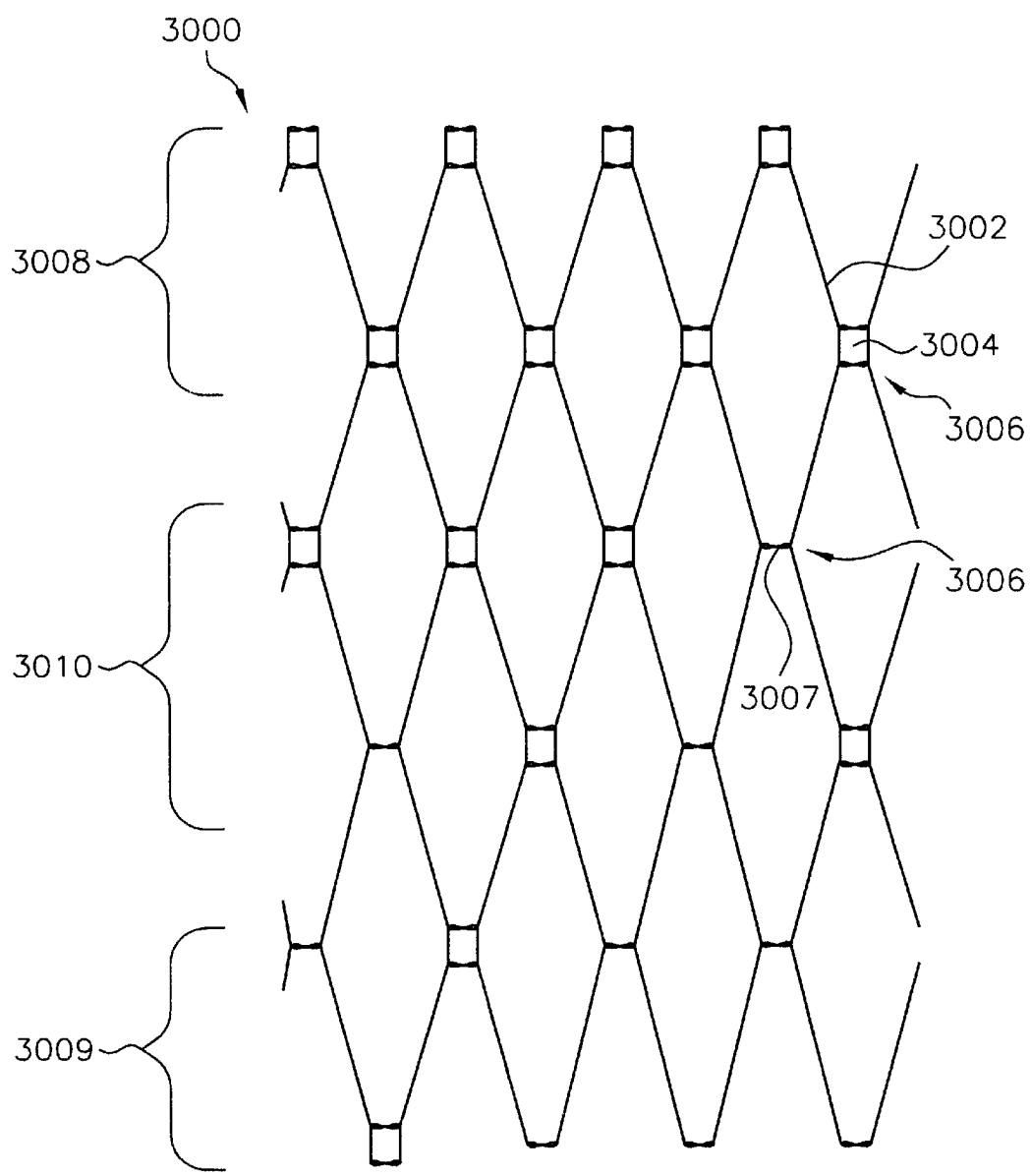
FIG. 12 is a plan view of an exemplary diamond stent embodiment where the stent has been cut along a line parallel to the stent axis and laid flat, showing a stent having a gradient of box nodes between a stiff region having a lot of box nodes and a more flexible region having fewer box nodes.

Another broad category of stent architecture is described in co-pending patent application [CIP of U.S. application Ser. No. 09/052,214] to Colgan et aL, (hereinafter "the Colgan Application") assigned to the assignee of the present invention, and incorporated herein by reference. Referring now to FIG. 12, the "diamond stent" 3000 described in the Colgan Application comprises a pattern of diamond-shaped elements 3002. The Colgan Application also discloses box nodes 3004 that may be placed at one or more interfaces 3006 between adjacent diamond elements. The Colgan Application discloses that box nodes 3004 may be used for providing local stiffness in one region as compared to another, such as greater stiffness at the ends than in the middle. Interfaces 3006 without box nodes comprise "empty interfaces" 3007. The present invention of modifying the stent architecture to provide a transition region between areas of different stiffness may be applied to the invention described in the Colgan Application, as may be the present invention of providing a stiffened region to mimic another region of a stent. Where a localized region 3008 is strengthened with a greater ratio of box nodes 3004 to empty interfaces 3007 as compared to another region 3009, a transition region 3010 may contain an intermediate ratio of box nodes to empty interfaces or a gradient in the ratio. As is shown in FIG. 12, region 3008 has a box node at every circumferential interface 3006, or a ratio of 4:0 box nodes to empty interfaces 3007, whereas region 3009 has only one box node per circumferential revolution, or a ratio of 1:3 box nodes to empty interfaces. Transition region 3010 contains an intermediate ratio of box nodes 3004 to empty interfaces 3007 in the form of a gradient of 3:1 to 2:2 box nodes to empty interfaces between from region 3008 with an infinite ratio and region 3009 with a 1:3 ratio. Region 3008 may be a mimic region that is stiffened using box nodes to provide stiffness and/or other manipulation properties that are essentially equivalent to the stiffness and/or other manipulation properties of another region of the stent.

Another technology known and described in the art for increasing the hoop strength of a stent, in particular the hoop strength of a braided stent, is described in U.S. Pat. No. 5,968,091 to Pinchuk et al. (hereinafter "the Pinchuk patent") and incorporated herein by reference. The Pinchuk patent describes a process for coating a stent with a polymer such that crossing or adjacent wire filaments are bound to each other by the polymer without the polymer occluding interstices between the filaments. The polymer is applied to the stent in a plurality of spray coatings, wherein an increase in the number of spray coatings increases the radial strength of the stent. The Pinchuk patent may be applied to selected sections of a stent to create stiffened regions and more flexible regions by applying the polymer coating in the stiff regions and no coating (or a lesser number of spray coats) in the flexible regions. The Pinchuk patent may further be applied to create transition regions between the relatively stiff and flexible regions by applying an intermediate number of spray coatings to the transition region between the flexible and stiff regions. A gradient transition region may be provided by creating a gradient number of coatings.

Figure 13:
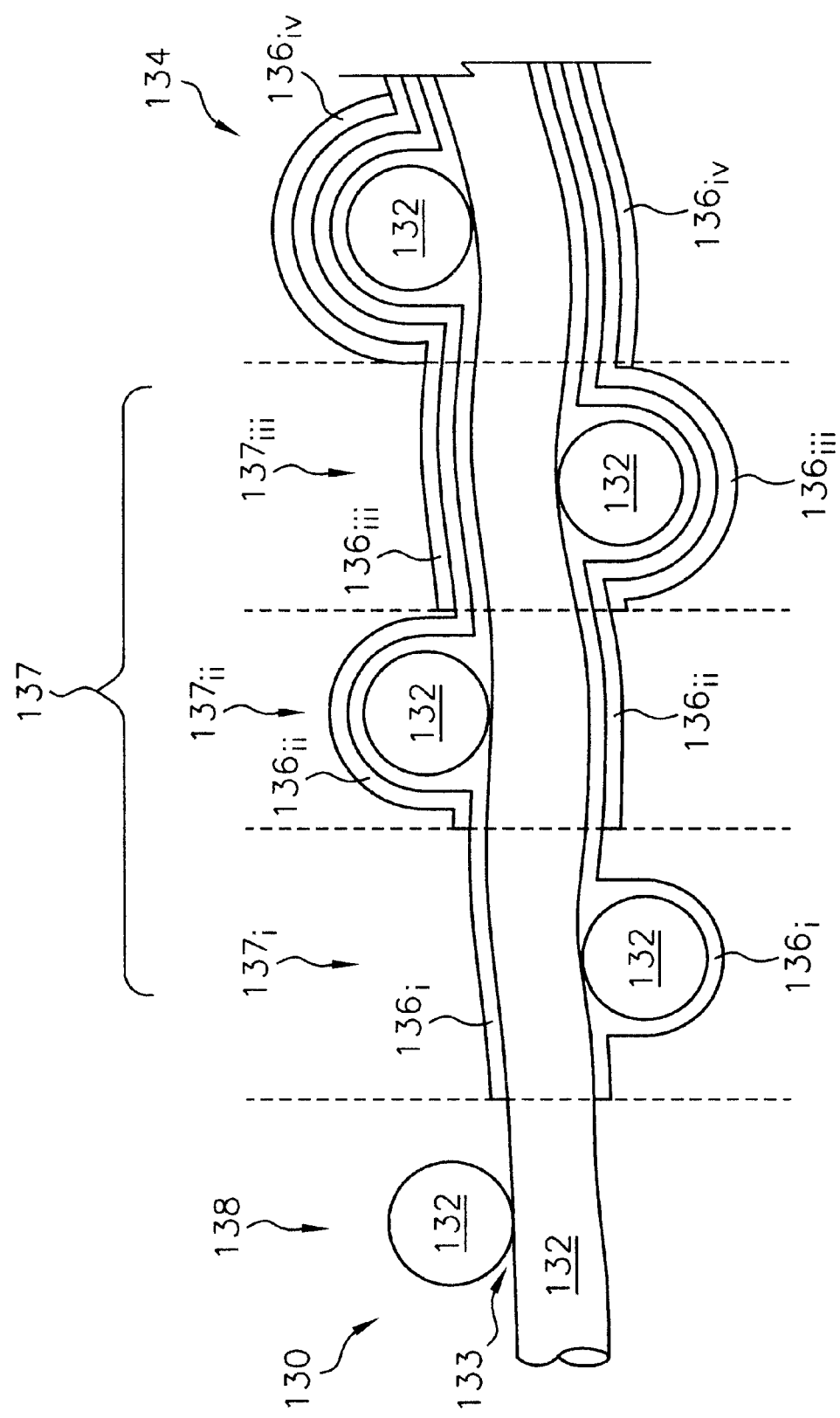
FIG. 13 is a longitudinal section of an exemplary braided stent having a polymer coating over the filaments of the stent to create a stiffened region, with a gradient number of spray coatings applied to provide a stiffness gradient between the relatively stiff and relatively flexible regions.

Thus, for example, referring now to FIG. 13 showing a longitudinal section of stent 130 comprising filaments 132 braided into a plurality of contact points 133, stiffened region 134 comprises four layers of polymer coating 136*i–iv*, whereas flexible region 138 comprises no coating layers. Transition region 137 comprises an intermediate number of layers of polymer coating from one layer 136*i* to three layers 136*i–iii*. Such layers may be applied by masking the region of the stent not to be coated during spray coating of each region. Thus, for the application of coating 136*i*, only flexible region 138 is masked, for application of coating 136*ii*, flexible region 138 and transition region 137*i* is masked, for application of coating 136*iii*, flexible region 138 and transition regions 137*i* and 137*ii* are masked, and for application of coating 136*iv*, flexible region 138 and all of transition region 137 (137*i–137iii*) is masked. The end result is that the coating in stiffened region 138 is thicker than in flexible region 138 (which may also have one or more coats, but just fewer coats than stiffened region 138) and that there is an intermediate, gradient coating thickness in transition region 137. Other methods of applying the coating to the wire may also be used.

Although the polymer coating method of stiffening is particularly advantageous for stiffening braided stents or for affixing adjacent apices of zig-zag stents as disclosed in the Pinchuk patent, the polymer stiffening method may be applied to any stent architecture known in the art having overlapping, touching, or nearly-touching filaments desired to be bonded together with some degree of stiffness. Although shown with respect to a braided stent having contact points 133 in FIG. 13, the polymer coating is applicable to stents having only near-contact points, a near-contact contract point being defined as a point where stent filaments do not actually cross or contact one another, but are close enough that the polymer can bridge the distance between the filaments. Furthermore, as is well-known in the art, filamentary stent architectures have some degree of interstitial space defined by the filaments. The interstitial space may be in the form of discrete closed cells bounded on all sides by filamentary structure, or a continuous open space connected by the gaps between near-contact points. The polymer coating method of the present invention, as described in the Pinchuk patent, does not substantially occlude the interstitial space. That is, a majority of the interstitial space still remains after the coating process, even if the coating process may segment a formerly continuous open space into discrete cells by closing gaps between near-contact points.

While the present invention has been described with respect to specific embodiments thereof, it is not limited thereto. Therefore, the claims that follow are intended to be construed to encompass not only the specific embodiments described but also all modifications and variants thereof which embody the essential teaching thereof.

What is claimed:

1. A modular elongated stent for holding open a body lumen and for assembly in situ, the stent comprising at least a first component and a second component, the stent having an assembled configuration comprising the first component and the second component assembled together, the stent comprising:

an overlap region in the first component adapted to receive a portion of the second component in the assembled configuration, the overlap region having a first set of manipulation properties in the assembled configuration;

one or more flexible regions attached to the overlap region, each flexible region having a second set of manipulation properties different than the first set of manipulation properties, the second set of manipulation properties comprising at least one property selected from the group consisting of: greater flexibility than the first set of manipulation properties, greater kink resistance than the first set of manipulation properties, or less radial strength than the first set of manipulation properties;

a mimic region attached to the flexible region, the mimic region having a third set of manipulation properties that is essentially equivalent to the first set of manipulation properties; and at least one transition region between the mimic region and the flexible region adapted to have an intermediate set of manipulation properties between the first set of manipulation properties and the second set of manipulation properties, the at least one transition region comprising a bridging material attached to the stent, the bridging material comprising a discrete portion thereof extending into the mimic region.

2. A modular elongated stent for holding open a body lumen and for assembly in situ, the stent comprising at least a first component and a second component, the stent having an assembled configuration comprising the first component and the second component assembled together, the stent comprising:

the first component, comprising a trunk section, a bifurcated section attached to the trunk section and having a first branch comprising a socket and a second branch comprising a fixed leg interface, and a fixed leg section depending from the fixed leg interface, the trunk section and the fixed leg section comprising flexible regions, wherein the trunk section and the fixed leg section are integrally and non-modularly connected to one another at the fixed leg interface;

the second component, comprising a modular leg component having a mating portion adapted for inserting in the socket in the assembled configuration, the socket and mating portion in the assembled configuration comprising an overlap region; and the overlap region having a first set of manipulation properties and the flexible regions having a second set of manipulation properties different than the first set of manipulation properties, the second set of manipulation properties comprising at least one property selected from the group consisting of: greater flexibility than the first set of manipulation properties, greater kink resistance than the first set of manipulation properties, or less radial strength than the first set of manipulation properties;

wherein the first component comprises a mimic region in the fixed leg interface having a third set of manipulation properties that is essentially equivalent to the first set of manipulation properties.

3. The stent of claim 2 wherein the mimic region comprises reinforcing material attached to the stent.

4. The stent of claim 3 herein the reinforcing material comprises an overlapping stent.

5. The stent of claim 3 wherein the reinforcing material comprises one or more stiffening filaments.

6. The stent of claim 2 further comprising a transition region between the fixed leg and the fixed leg interface and a transition mimic region in the modular leg component adjacent the mating portion, the transition region comprising an intermediate set of manipulation properties between the second set of manipulation properties and the third set of manipulation properties and the transition mimic region comprising a fourth set of manipulation properties essentially equivalent to the intermediate set of manipulation properties.

7. A modular elongated stent for holding open a body lumen and for assembly in situ, the stent comprising at least a first component and a second component, the stent having an assembled configuration comprising the first component and the second component assembled together, the stent comprising:

an overlap region in the first component adapted to receive a portion of the second component in the assembled configuration, the overlap region having a first set of manipulation properties in the assembled configuration;

one or more flexible regions attached to the overlap region, each flexible region having a second set of manipulation properties different than the first set of manipulation properties, the second set of manipulation properties comprising at least one property selected from the group consisting of: greater flexibility than the first set of manipulation properties, greater kink resistance than the first set of manipulation properties, or less radial strength than the first set of manipulation properties;

a mimic region attached to the flexible region, the mimic region having a third set of manipulation properties that is essentially equivalent to the first set of manipulation properties; and a transition region between the flexible region and the mimic region, the transition region comprising an intermediate set of manipulation properties between the second set of manipulation properties and the third set of manipulation properties.

8. The stent of claim 7 wherein the transition region comprises a gradient of manipulation properties from the second set of manipulation properties to the third set of manipulation properties.

9. The stent of claim 8 wherein the transition region comprises a bridging material attached to the stent between the mimic region and the flexible region.

10. The stent of claim 9 wherein the bridging material comprises one or more wires attached to the stent.

11. A modular elongated stent for holding open a body lumen and for assembly in situ, the stent comprising at least a first component and a second component, the stent having an assembled configuration comprising the first component and the second component assembled together, the stent comprising:

an overlap region in the first component adapted to receive a portion of the second component in the assembled configuration, the overlap region having a first stiffness in the assembled configuration;

one or more flexible regions attached to the overlap region, each flexible region having a second stiffness less than the first stiffness; and a mimic region attached to the flexible region, the mimic region having a third stiffness essentially equivalent to the first stiffness, the stent further comprising a transition region between the flexible region and the mimic region, the transition region comprising an intermediate stiffness greater than the second stiffness and less than the third stiffness.

12. The stent of claim 11 wherein the transition region comprises a stiffness gradient from the second stiffness to the third stiffness.

13. An elongated stent for holding open a body lumen, the stent comprising:

at least one stiff region having a first set of manipulation properties;

at least one flexible region having a second set of manipulation properties different than the first set of manipulation properties, the second set of manipulation properties comprising at least one property selected from the group consisting of: greater flexibility than the first set of manipulation properties, greater kink resistance than the first set of manipulation properties, or less radial strength than the first set of manipulation properties; and at least one transition region between the stiff region and the flexible region adapted to have an intermediate set of manipulation properties between the first set of manipulation properties and the second set of manipulation properties, the at least one transition region comprising a bridging material attached to the stent, the bridging material comprising a discrete portion thereof extending into the at least one stiff region.

14. The stent of claim 13 wherein the transition region comprises a gradient between the first set of manipulation properties and the second set of manipulation properties.

15. The stent of claim 14 wherein the bridging material comprises one or more filaments attached to the stent.

16. The stent of claim 15 wherein the attached filaments comprise wires welded to the stent.

* * * * *